United States Patent [19]
Yoshida et al.

[11] 4,205,685
[45] Jun. 3, 1980

[54] THERMOGENIC SHEET-COMBINED POULTICES

[75] Inventors: Risaburo Yoshida; Keisuke Kaiho; Yusaku Ide, all of Tokyo; Kanji Noda, Chikushino; Tetsuya Yamagata, Tosu; Hirotaka Kida, Fukuoka, all of Japan

[73] Assignees: Hisamitsu Pharmaceutical Co., Ltd., Tosu; Toyo Ink Manufacturing Co., Ltd., Tokyo, both of Japan

[21] Appl. No.: 839,240

[22] Filed: Oct. 4, 1977

[30] Foreign Application Priority Data

Oct. 6, 1976 [JP] Japan .................... 51-119319

[51] Int. Cl.² ............................ A61F 7/00; A61F 7/04
[52] U.S. Cl. ................................................. 128/399
[58] Field of Search ............... 128/403, 399, 401, 402, 128/268; 126/283, 400, 263; 252/70; 44/3 R, 3 A, 3 C; 424/73; 422/511

[56] References Cited
U.S. PATENT DOCUMENTS

| | | | |
|---|---|---|---|
| 696,441 | 4/1902 | Holmes | 128/268 |
| 1,525,168 | 2/1925 | Davidson | 126/263 UX |
| 1,819,807 | 8/1931 | Baysinger | 128/403 |
| 2,629,378 | 2/1953 | Barton | 128/268 |
| 2,710,008 | 6/1955 | Jensen | 128/403 |
| 3,951,127 | 4/1976 | Watson et al. | 128/399 |
| 3,976,049 | 8/1976 | Yamashita et al. | 128/403 |
| 4,106,478 | 8/1978 | Higashijima | 128/403 |
| 4,114,591 | 9/1978 | Nakagawa | 128/403 |

*Primary Examiner*—Robert W. Michell
*Assistant Examiner*—Milford Juten
*Attorney, Agent, or Firm*—Jordan and Hamburg

[57] ABSTRACT

A thermogenic sheet combined poultice comprising a thermogenic composition layer capable of generating heat in the presence of air or oxygen and a heat-stable wet pack composition layer; and a process for the production of the thermogenic sheet combined poultice.

10 Claims, 2 Drawing Figures

THERMOGENIC SHEET-COMBINED POULTICES

The present invention relates to a thermogenic sheet-combined poultice and a process for producing the same.

The thermogenic sheet combined poultice is one of medicines for thermotherapy and also called moist or wet heat pack. Thermotherapies for curing an affected or sore part of the body by applying heat to said part from the outside have long been used and, among others, application of towel wetted with hot water to the affected part of the body is familiar to us as the simplest thermotherapy. Nowadays, there are various types of thermotherapies, which include superficial heat stimulation such as infra-red radiation, lightning bath, hot compress, Sauna bath, cauterization method, byssocausis, hot bath, steam bath, steam compress, hot compress, alternating bath, foam bath, swirling bath, vibrating bath, mud bath, Havart tank, kinetotherapeutic bath, hydro-electric bath, medicinal spring bath and paraffin bath, and also include profound heat stimulation such as short-wave, ultra-short-wave and supersonic therapies. In hospitals and the like, there are very often used poultices such as HOT PACK (trademark) comprising a bag filled with a dispersion of starch and ONSHIPPU (trademark) comprising a thermogenic pad using electricity, the HOT PACK being useful in warming the affected part of the bodies by heating the bag with a heating source such as hot water and applying the heated bag to said affected part while the ONSHIPPU being useful in warming the affected part with the thermogenic pad. Even at the present, typical of hot pack therapy which is one of thermotherapies, is warming of the affected part by applying heated wet towel thereto as mentioned before and no improved hot pack therapy is developed yet although there have been developed various appliances and utensils for use in other thermotherapies. The reason for this is that all of presently marketed poultices or wet pack compositions are mainly used for cold pack and they are only indicated in their directions to be usable as a substitute for hot pack if warmed with hot water. Thus, they are not so effective as a hot pack composition and they will keep themselves hot for a period of time of as short as only about 10 minutes if warmed with hot water, thereby making it impossible to use them as a satisfactory hot pack composition.

Thermotherapy which raises the temperature of skin of the bodies, enlarges the blood vessels and promotes the blood circulation to promote metabolism, lower muscle tone and enable accelerate absorption of effective ingredients in a short time and which has analgetic, anti-spasmodic and anti-inflammatory effects, is a very important therapy and, therefore, satisfactory thermogenic sheet combined poultices have heretofore been sought to be developed.

In attempts to develop thermogenic sheet combined poultices comprising (1) a thermogenic composition in sheet form which is capable of maintaining heat for a satisfactorily long time, adjusting the temperature obtained from the heat to a desired level and being easily handled and (2) a wet pack composition which is stable to heat, the present inventors made various studies and, as a result of their studies, it has been found that (1) a thermogenic composition comprising alkali metal sulfides or polysulfides or hydrates thereof and carbonaceous material or iron carbide, the sulfur compound and the carbon compound being reacted with air in the presence of the carbon compound, is combined with (2) a wet pack composition stable to heat, thereby to form a simplified and highly effective thermogenic sheet combined poultice. This invention is based on this finding.

The thermogenic sheet combined poultices comprise a thermogenic sheet capable of generating heat when contacted with oxygen or air and a wet pack composition layer stable to heat. More particularly, the thermogenic sheet comprises (A) at least one sulfur compound selected from the group consisting of alkali metal sulfides and polysulfides and hydrates thereof and (B) at least one carbon compound selected from the group consisting of carbonaceous materials and iron carbide, and it will generate heat when in contact with oxygen or air; the heat-stable wet pack composition layer comprises a heat-stable base or main ingredient for wet pack, other ingredients therefor and, if desired, a medicine.

Japanese Patent Application Laying-Open Gazettes Nos. 54187/75 and 54188/75 disclose thermogenic wet pack compositions containing a thermogenic composition. The thermogenic compositions of said known wet pack compositions contain iron powder as the main ingredient and will generate heat when contacted with oxygen or air and water. Thus, these known thermogenic compositions are remarkably different from those used in the present invention. In addition, said two Gazettes describe nothing about a wet pack composition layer which is suitable for lamination with the thermogenic composition.

On the other hand, the thermogenic sheet combined poultices of the present invention having the constitution as previously mentioned, are simple ones which will generate heat only by contact with oxygen or air substantially without troubles such as thermal destruction and decomposition.

The present invention will be explained in more detail hereinbelow.

First of all, the thermogenic sheet will be detailed. The thermogenic composition used herein comprises a mixture of the following ingredients:

(1) at least one member selected from the group consisting of sulfides and polysulfides of alkali metals such as Li, Na, K, Rb and Cs, and hydrates of said sulfides and polysulfides (the at least one member (1) being hereinafter referred to as "ingredient A"), and (2) at least one member selected from the group consisting of iron carbide and carbonaceous materials such as carbon black, activated carbon, charcoal, coal, coke, pitch, asphalt and graphite (the at least one member (2) being hereinafter referred to as "ingredient B").

The ingredients A and B will be mixed together to generate heat by being contacted with air or pure oxygen or by being incorporated with a material capable of producing oxygen by chemical reaction. The iron carbide may be obtained by, for example, a process disclosed in Japanese Patent Application Laying-Open Gazette No. 22000/75.

In hot pack therapy, it is suitable to apply to an affected part of the body a wet pack heated to usually 40°–60° C., preferably 45°–55° C. Application of a wet pack at lower than 40° C. will not exhibit satisfactory cure, while application thereof at higher than 60° C. will not be desirable since the use of such a high temperature does not permit patients to undergo the cure and causes burn, scald or the like.

The duration of hot condition of the wet pack is suitably from 15 minutes to 6 hours, preferably from 1 to 3 hours. The duration of less than 15 minutes will be insufficiently effective in hot pack treatment, whereas the duration of more than 6 hours will be undesirable because of problems as to the degree of drying of the wet pack composition, side effects due to continuous heating of the affected part and the time within which almost all of the medicine in the wet pack is absorbed.

The blending ratio between the ingredients A and B should be determined in view of the thermogenic efficiency and the desired temperature to be used at the time of hot pack therapy. The ratio by weight of ingredient A to ingredient B is in the range of 10–90/90–10, preferably from 40/60 to 60/40. A blend of the ingredients A and B in said ratios may usually be used in an amount of 10–40 g, preferably 20–30 g, in an area of 8 cm×12 cm thereby to obtain the desired temperature and high thermogenic efficiency.

In order to inhibit sharp changes in temperature due to heat generation and radiation, various heat-stable fillers (ingredient C) may be added to a blend of the ingredients A and B. Examples of these fillers are natural cellulosic fragments such as wood dust and linter, synthetic fibers in fragmentary form such as polyester fibers, scrap of foamed plastics such as foamed polystyrene and polyurethane, and inorganic compounds such as silica powder, porous silica gel, sodium sulfate, barium sulfate, iron oxide and alumina. The ingredients C may be used in a ratio between the ingredient C and the total of ingredients A and B of from 0/100 to 90/10, preferably from 20/80 to 70/30. In addition, it is preferable to have the thermogenic composition according to the present invention contain natural cellulosic fragments as the filler.

The thermogenic rate and the duration of warming may be adjusted by varying, for example, the area at which the thermogenic composition is contacted with air or oxygen; more particularly, they may be adjusted by selecting the kind composition and particle size of the ingredients A and B, the amount of inflow of air or oxygen, the kind and amount of fillers, and the like. In the present invention, the particle size of the ingredients A and B is in the range of 10–100 mesh, preferably 30–50 mesh, and these ingredients, together with the ingredient C if necessary, may be powdery or may be formed to granules, pellets, sheets or any other desired shapes. The area of contact with air or oxygen may be 0.5–10 $cm^2/96\ cm^2$, preferably 2–5 $cm^2/96\ cm^2$.

Means for contacting the thermogenic composition with air or oxygen are illustrated below.

The thermogenic composition is encased in an airtight container such as a plastics film-made or metallic foil-made container and perforating the container; it is encased in a container of an air-permeable material such as paper, cloth or an air-permeable resin film; and it is encased in a sufficiently air-permeable inner container which is housed in an airtight outer container provided with an air inlet capable of being opened or closed as required. Inter alia, the containers made of cloth or the air-permeably worked resin film may preferably be used because of their air permeability.

Since it is possible to allow the thermogenic composition used herein to generate heat or stop heat generation by contacting the thermogenic composition with, or preventing contact thereof with, air or oxygen, it is accordingly possible to discontinue or resume cure with the thermogenic sheet combined poultice.

The material for the container of the thermogenic composition is selected depending the manner in which the thermogenic composition is contacted with air or oxygen; natural fibers, synthetic fibers, plastics films and the like are widely used, and it is desirable to use a highly heat-conductive material as a part or the whole of the material for the container.

The thermogenic composition may be used after being encased in a bag, a housing having many compartments defined by air-permeable partitions, or the like. It may preferably be used in sheet form. In encasing the thermogenic composition, it is necessary to effect the step of blending the ingredients A and B together and the subsequent steps in the absence of air or oxygen and, of course, in the presence of an inert gas such as nitrogen, argon or carbonic acid gas.

There will now be detailed the heat-stable wet pack composition in layer or sheet form.

As previously mentioned, the wet pack composition used in the present invention are classified into two types:

(1) Wet pack composition consisting of a base ingredient for wet pack, other ingredients necessary therefor and a medicine for wet pack, and (2) Wet pack composition consisting of a base ingredient for wet pack and other ingredients necessary for wet pack (without such a medicine). The term "other ingredients necessary for wet pack" is intended not to contain a medicine for wet pack throughout the specification and claims.

The wet pack composition (1) containing a medicine for wet pack is usually used, but the use of even the wet pack composition (2) (without such a medicine) in the manufacture of a thermogenic sheet combined poultice will produce the thermogenic sheet combined poultice which exhibits satisfactory wet pack effects contemplated by the present invention.

The wet pack compositions (1) and (2) will be detailed hereinbelow.

In the wet pack compositions (1) and (2), the base ingredients for wet pack include kaolin, bentonite, talc, wax, vaselin, sodium lactate, zinc oxide, boric acid, aluminum silicate or a mixture thereof. The other ingredients necessary for wet pack are tackifiers, softening agents, wetting agents and the like. Typical of the other ingredients are sodium alginate, methylcellulose, carboxyvinyl, polymers, carboxymethylcellulose, ethylcellulose, polyvinyl pyrrolidone, polyvinyl alcohol, polyvinyl methyl ether, sodium polyacrylate, tragacanth gum, atactic polypropylene, guaiacol, ester gum, natural gum latex, gelatine, liquid paraffin, silicone, glycerine, propylene glycol, polyethylene glycol, diethyl glycol monoethyl ether, magnesium oxide, sorbitol, xylitol, urea, aluminum acetate, beryllium hydroxide, magnesium hydroxide, calcium hydroxide, barium hydroxide, water and mixtures thereof.

The wet pack composition used in the present invention may preferably comprise kaolin, zinc oxide, gelatine, carboxymethylcellulose, sodium polyacrylate, glycerine, sorbitol, water, water or a mixture thereof because of their heat stability.

The medicines for wet pack used herein include methyl salicylate, salicylic acid glycol, salicylic acid, menthol, peppermint oil, camphor, thymol, creosote, taurine, extract of scopolia, diphenhydramine hydrochloride, diphenhydramine, mercurochrome, burn phellodendron bark pickled plum flesh, Japanese pepper oil, borneol, epirocaine and mixtures thereof, with methyl salicylate, menthol, camphor, thymol, peppermint oil and the like being particularly preferred.

The wet pack composition (1) comprises, by weight, 3–20 parts of the base ingredient for wet pack, 76–96 parts of the other ingredients such as tackifiers, softening agents and wetting agents and 1–4 parts of a medicine for wet pack.

The wet pack composition (2) comprises, by weight, 2–21 parts of the same base ingredient as above and 79–97 parts of the same other ingredients as above.

It is necessary that the ingredients respectively weighed out as required be blended and kneaded to form a pasty plaster thereof. To this end, the order in which they are blended with each other should suitably be selected. For example, a suitable amount of the base material for wet pack is incorporated with the other necessary ingredients such as the tackifier, softening agent and wetting agent, on a stirrer. The resulting mixture is then kneaded under heat on the mixer to obtain a pastry plaster (wet pack composition (2)). In the case of manufacture of the wet pack composition (1), the medicine for wet pack is further added to, and kneaded with, said resulting mixture to obtain a pasty medicine-contained plaster. These compositions (1) and (2) are each spread to obtain a wet pack composition layer. The mixer used herein may be a non-high speed stirrer, but it may preferably be a high speed stirrer. The kneading may be effected at a temperature of about 20°–120° C. for 10–60 minutes. The medicines for wet pack may be kneaded with the base ingredient for wet pack and the other ingredients necessary therefor at the same time. The mixture so kneaded is spread and coated on a substrate, usually on one side of the encased thermogenic composition. The encased thermogenic composition, that is, the thermogenic sheet and the wet pack composition layer are produced separately from each other, and these sheet and layer may be laminated before being marketed or at the time of being used for cure. The substrates on which the kneaded mixture, that is, the wet pack composition is spread, include cloth, non-woven cloth, paper and synthetic resin films. The materials for the cloths include natural fibers such as silk, wool and cotton, artificial fibers such as staple fibers, viscose rayon and artificial silk, synthetic fibers such as nylon, polyester, acrylic, polyurethane fibers, and mixtures thereof. The cloths used may be ordinary non-napped cloths or napped cloths such as flannel and woolen cloth, with flannel and the like napped cloths being the most preferable.

The wet pack composition is spread and coated on one side of the thermogenic sheet or on a substrate to form thereon a layer which is then laminated or covered with a releasable film selected from plastics films such as Cellophane and polyethylene films. In this case, the releasable films may be those which have been coated with a releasing agent prior to their use.

In the accompanying drawings.

The heat stability, resistance to solubility in dermal secretion, and the like of the wet pack composition layer of the thermogenic sheet combined poultice of the present invention, will then be explained by reference to the test results shown in the following Table 1. In the following tests, the wet pack composition layer (1) used was one produced in Preparation 1 to be described later and the wet pack composition layer (2) was one produced in Example 7 to be also described later.

(1) Test for temperature characteristics:

(a) Viscosity under each temperature condition

Test method: One gram of each sample was charged into a Koka flow tester produced by Shimazu Works, Japan, allowed to stand under a load of 15 kg/cm$^2$ at a particular temperature for 20 minutes and then measured for viscosity.

The results are shown in the following Table 1.

Table 1

(Unit: poise)

| Sample | Temp. | | |
|---|---|---|---|
| | 40° C. | 50° C. | 60° C. |
| Poultice produced by A Co. | $3.16 \times 10^2$ | $1.58 \times 10^2$ | $0.88 \times 10^2$ |
| Poultice produced by B Co. | $1.00 \times 10^2$ or less | $1.00 \times 10^2$ or less | $1.00 \times 10^2$ or less |
| Wet pack composition layer (1) according to the present invention | $8.33 \times 10^2$ | $3.21 \times 10^2$ | $1.73 \times 10^2$ |
| Wet pack composition layer (2) according to the present invention | $8.25 \times 10^2$ | $3.15 \times 10^2$ | $1.65 \times 10^2$ |

As is apparent from the results shown in the above Table, the wet pack composition layers according to the present invention exhibited higher viscosity than the conventional poultices produced by Companies A and B. Thus, the wet pack composition layers used in the invention will retain their original shape without any troubles even when used as a hot wet pack.

In addition, wet pack compositions having a viscosity of less than $1.00 \times 10^2$ poise when used in the layer form, will usually cause the destruction and sagging of the layer thereby making it very often impossible to use them as a satisfactory wet pack composition layer.

(b) Change with the lapse of time under each temperature condition

Test method: Each sample encased in a bag was allowed to stand in a gear oven produced by Tabai Works, Japan and then tested for its shape retention period of time with the lapse of time. The shape retention period of time for each sample means the number of days for which the sample (like plaster) retains its original shape without it running out and collapsing.

The test results are shown in the following Table 2.

Table 2

| Sample | Temp. 40° C. | Temp. 50° C. |
| --- | --- | --- |
| Poultice produced by A Co. | 15 days | 3 days |
| Poultice produced by B Co. | 1–2 days | 1 day at longest |
| Wet pack composition layer (1) according to the present invention | At least 3 months | 2 months |
| Wet pack composition layer (2) according to the present invention | At least 3 months | " |

From the results shown in the above Table, it is apparent that the wet pack composition layers were much more excellent in heat stability with the lapse of time than the conventional poultices of Companies A and B.

(2) Test for resistance to solubility to dermal secretion

Secreted materials such as sweat tend to accumulate between a wet pack composition and the skin to which this composition is applied, thereby causing stickiness on the skin and the destruction of the wet pack composition or plaster. Such a tendency is, of course, more remarkable in the practice of hot wet pack. Thus, the purpose of the test is to measure the water solubility resistance of each of conventional poultices and wet pack composition layers thereby to know the effect thereof on dermal secreted materials.

(a) Solubility in water

Test method: Each of sampled plasters was spread in a predetermined area and allowed to stand under a fixed temperature condition and then under a humidity varying from a low level to a high level, after which the samples were measured for amount of water absorbed and dissipated thereby to find the humidity or transitional humidity at which the weight of the sample increased or decreased. The water solubility of each of the samples was inferred from the level of the transitional humidity of the sample. The results are shown in Table 3.

Table 3
(Unit: %)

| Sample | Temp. 40° C. | Temp. 50° C. |
| --- | --- | --- |
| Poultice produced by A Co. | 83 | 77 |
| Poultice produced by B Co. | 73 | 50 at hi |
| Wet pack composition layer (1) according to the present invention | 88 | 83 |
| Wet pack composition layer (2) according to the present invention | 86 | 80 |

From the results shown in the above Table, it is considered that the water solubility of the wet pack composition layers according to the present invention is very low since they exhibited a higher transitional humidity at which they began to absorb water, than the conventional poultices produced by Companies A and B.

(b) Solubility in warmed water

Test method: Each of sampled plasters were introduced into warmed water at a temperature from 50° to 80° C. The resulting aqueous solutions or dispersions were measured for white turbidity. The results are indicated in the following Table 4.

Table 4

| Sample | Temp. 50° C. | 60° C. | 70° C. | 80° C. |
| --- | --- | --- | --- | --- |
| Poultice produced by A Co. | None | Slight white turbidity | Slight white turbidity | White turbidity |
| Poultice produced by B Co. | Remarkable white turbidity | Remarkable white turbidity | Remarkable white turbidity | Remarkable white turbidity |
| Wet pack composition layer (1) according to the present invention | None | None | None | Slight white turbidity |
| Wet pack composition layer (2) according to the present invention | None | None | None | Slight white turbidity |

From the above results, it is apparent that as compared with the conventional poultices produced by Companies A and B, the wet pack composition layers according to the present invention had very little risks of being dissolved in the warmed water and were, therefore, excellent in water-proofing.

The above results obtained from the tests for temperature characteristics and water solubility resistance clearly show that as compared with the conventional poultices, the wet pack composition layers according to the present invention were superior in every respect and had very little risks of destruction and running-out of the layer as well as of dissolution thereof in the sweat and the like, whereby they are considered to be very suitable as a wet pack composition layer for the thermogenic sheet-combined poultice of the present invention.

The promotion of absorption of the medicines, which is one of the features of the present invention, will be explained hereinbelow by reference to the experiment results to be described later.

METHOD OF EXPERIMENT

Samples

As the samples there were used the thermogenic sheet combined poultices of the present invention (hereinafter called "novel poultice") each consisting of the thermogenic sheet and the wet pack composition layer, the novel poultices being ones produced in Example 4. For comparison, only the same wet pack composition layers (hereinafter called "control") as above were used as the controls.

Subject and Dosing

Five healthy adult men each weighing about 65 kg, were administered in the following manner. First of all, an aluminum sheet was applied to the cloth surface of each of the controls. Two controls so applied were each applied directly to the back of each of the subjects by securing the periphery of the controls thereto with an adhesive tape. Six hours after the application of the controls, they were removed from the back of the subjects and portions of the wet pack composition of the control remaining on the back were wiped off with ethanol.

One week later, two novel poultices were each applied directly to the back of each of the same subjects by securing the periphery of the poultices thereto with an adhesive tape without clogging the gas inlets of the thermogenic sheet. The novel poultices so applied were removed from the back six hours after their application.

Collection of blood and urine samples, and assay of total salicylates in blood and urine Prior to the experiments, about 10 ml of blood and about 50 ml of urine were collected from the subjects and used as the controls at the time of subsequent assay.

In each of the experiments, about 5 ml of blood were collected from the ante-cubital vein 0.5, 1, 2, 3, 4, 5 and 12 hours after the application of the sample. The blood so collected was centrifugalized to obtain serum a part of which was assayed for total salicylic acid derivatives. Urine was cumulatively collected 3, 6, 12 and 24 hours after the application of the sample, and a part of each of the cumulatively collected urine portions was assayed for total salicylic acid derivatives.

In the practice of the assays, the metabolites of methyl salicylate in the serum and urine so collected were hydrolyzed with an acid at 100° C. for 16 hours to salicylic acid. After the salicylic acid so produced was dissolved and extracted, it was further extracted with an aqueous solution of an alkali and measured for intensity of fluorescence at a pH of 10.6 and at an excitation wavelength of 300 nm and a measurement wavelength of 405 nm. The measurement for fluorescence intensity was effected by the use of a Hitachi fluorescence spectrophotometer (Model 204).

Results of experiments

Figure 1:
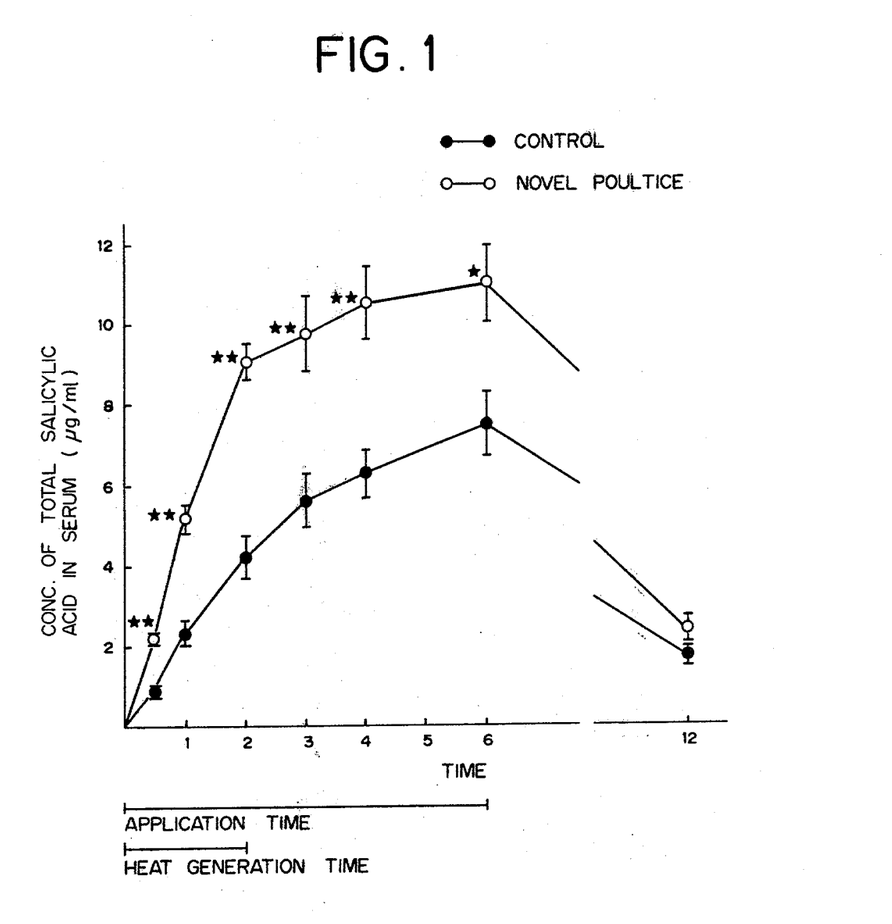
FIG. 1 shows graphs indicating the concentrations of total salicylic acid derivatives expressed in terms of salicylic acid with the lapse of time and FIG. 2 shows graphs indicating the cumulative amounts of total salicyclic acid derivatives excreted in urine, in percent of the amount of medicine applied.
Figure 2:
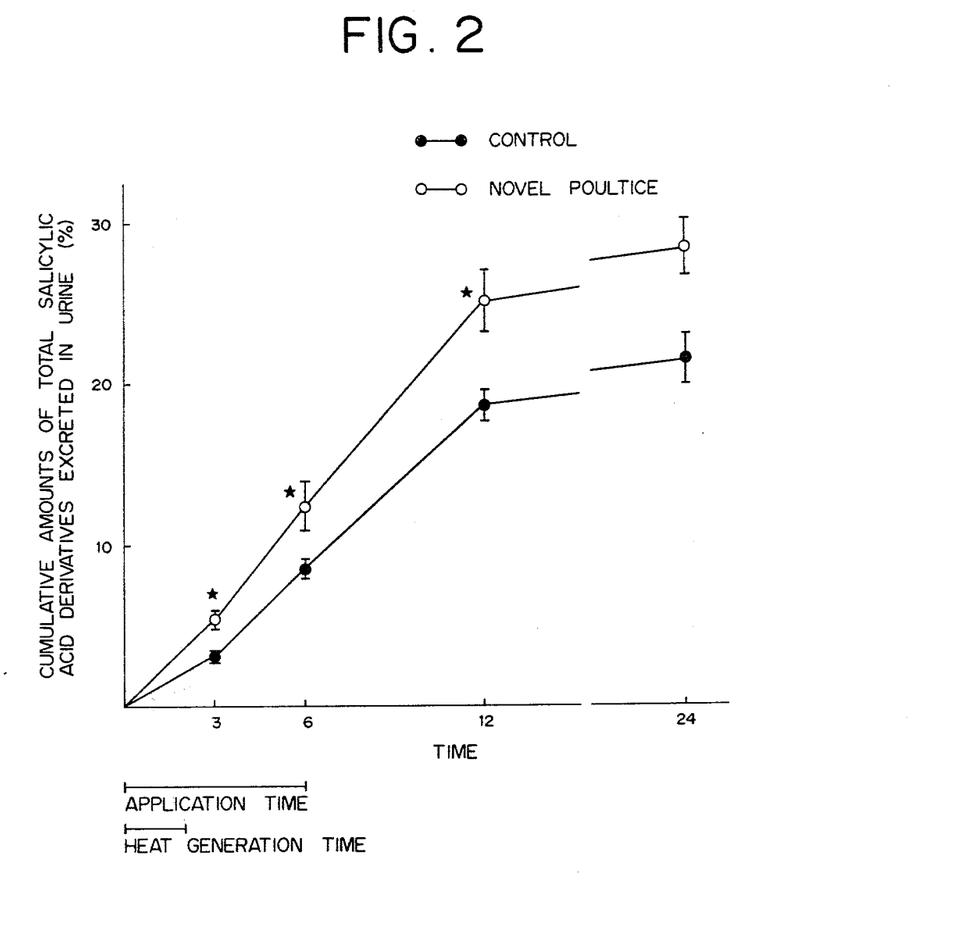

FIG. 1 shows the results obtained from the assay of total salicylic acid derivatives in the serum in terms of salicylic acid. From the figure it is seen that the concentration of the total derivatives in the present invention was about twice as high as that in the comparative case using the control during the first two hours during which the thermogenic sheet generated heat and that the former concentration was still significantly higher than the latter during the subsequent 4 hours, whereby the promotion of absorption of the medicine by the use of the novel poultice (containing the thermogenic sheet) of the present invention was proved. FIG. 2 shows the cumulative amounts of total salicylic acid derivatives excreted in urine in percent of the amount of medicine applied. From FIG. 2 it is seen that the amounts excreted in the present case were 1.3–1.8 times as large as those in the comparative case using the control, thereby indicating the promotion of absorption of the medicine in the former case. Further, in FIGS. 1 and 2, the plotted points represent the "average values±standard error" for the five subjects, the single asterisk * indicates the significant difference of a risk of 5% and the double asterisks ** the significant difference of a risk of 1%.

There will now be explained the temperature and heat duration attained by heat generation of the thermogenic sheet according to the present invention with respect to the amount of thermogenic composition used and the porosity of the case holding this composition therein, by reference to the following reference examples.

REFERENCE EXAMPLE 1

Sample

The procedure of Example 1 to be described later was followed except that 30 g and 20 g of the thermogenic composition were applied respectively to areas 8×12 cm and the porosity of a polyethylene film-made case was varied, to produce the same thermogenic sheets (encased thermogenic composition layers) as produced in Example 1. Separately, the same wet pack composition layers as produced in Preparation 1 were produced in the same manner as in Preparation 1. The thermogenic sheet and wet pack composition layer so produced were then laminated or combined with each other to obtain a sample to be tested. The samples were enclosed or wrapped in an air-impermeable packing material.

Test method

The samples were each taken out of the packing material and applied to a stainless steel plate adjusted to 37° C. with the wet pack composition layer facing to the plate to measure the temperature of the surface portion of said layer applied by the use of a surface thermometer, thus finding both a uniform temperature attained by heat generation of the thermogenic layer and duration of the uniform temperature. The results are shown in Table 5.

In this Reference example and the following Reference examples and Examples, the perforated polyethylene films used for wrapping the thermogenic composition layer therein were 70μ in thickness, the polyethylene films used as a liner for the wet pack composition layer 20 to 25μ in thickness, and the wet pack composition layer 1 to 3 mm in thickness, unless otherwise indicated.

Table 5

| Amount of thermogenic composition used (g) | Porosity of polyethylene film (%) | Temp. attained by heat generation (°C.) | Duration (hr) |
|---|---|---|---|
| 30 | 2.0 | 40 | 4 |
| " | 2.5 | 45 | 3 |
| " | 3.0 | 50 | 2 |
| " | 3.5 | 55 | 1 |
| " | 4.0 | 60 | 0.5 |
| 20 | 2.0 | 40 | 2 |
| " | 2.5 | 45 | 1 |
| " | 3.0 | 50 | 0.5 |

REFERENCE EXAMPLE 2

Sample

There was produced an encased thermogenic composition layer (or thermogenic sheet) having the same composition as Example 2 to be described later, in the same manner as in Reference example 1. Separately, there was produced a wet pack composition layer having the same composition as Example 2 in the same manner as in Example 2. The encased thermogenic composition layer and wet pack composition layer so produced were laminated or combined together to obtain a sample to be tested.

Test method:

The test method used was the same as that used in Reference example 1.

The results are indicated in the following Table 6.

Table 6

| Amount of thermogenic composition used (g) | Porosity of polyethylene film (%) | Temp. attained by heat generation (°C.) | Duration (hr) |
|---|---|---|---|
| 30 | 2.0 | 36 | 4 |
| " | 2.5 | 40 | 3 |
| " | 3.0 | 45 | 1.5 |
| " | 3.5 | 51 | 0.5 |
| " | 4.0 | 59 | 0.2 |
| 20 | 2.0 | 36 | 2 |
| " | 2.5 | 41 | 0.6 |
| " | 3.0 | 45 | 0.2 |

REFERENCE EXAMPLE 3

Sample

An encased thermogenic composition layer having the same composition as Example 3 to be described later was produced in the same manner as in Reference example 1 and, separately, a wet pack composition layer having the same composition as Example 3 was produced in the same manner as in said Preparation. These layers so produced were combined with each other to obtain a sample to be tested.

Test method

The test method of Reference example 1 was followed. The results are shown in the following Table 7.

Table 7

| Amount of thermogenic composition used (g) | Porosity of polyethylene film (%) | Temp. attained by heat generation (°C.) | Duration (hr) |
|---|---|---|---|
| 30 | 2.0 | 43 | 3.5 |
| " | 2.5 | 47 | 2.5 |
| " | 3.0 | 53 | 1.5 |
| " | 3.5 | 59 | 0.5 |
| " | 4.0 | 63 | 0.3 |
| 20 | 2.0 | 42 | 1.5 |
| " | 2.5 | 47 | 0.6 |
| " | 3.0 | 53 | 0.2 |

As previously mentioned, the novel poultices of the present invention comprise a thermogenic sheet (encased thermogenic composition layer) and a heat-stable wet pack composition layer. They are advantageous in that they are very expedient for use in cure or treatment and effective in absorption of the effective ingredients into the body in a short time, for example.

The thermogenic sheet combined poultice of the present invention, as mentioned above, may be used as material for thermotherapy to exert analgetic, antispasmodic and anti-inflammatory actions. More particularly, application of the thermogenic sheet combined poultice may have particularly good effects on the treatment of neuralgia, arthrorheumatism, tendosynovitis, arthritis, lumbago, degeneration of intervertebral disc, fibrosis of brachial subscapularis, muscular pain, gonalgia, contusion, sprain, fracture, headache, whiplash syndrome, gastric pain, constipation, feeling of cold, omarthritis, degenerative arthropathy, atrophy of articulation and the like at their chronic stage. However, application of the poultice of the present invention is not preferable to treat therewith pyogenic diseases caused by bacterial infection, diseases accompanying high fever, diseases under bleeding, and the like.

The poultice of the present invention may preferably be applied in an amount of 14 cm×10 cm from one to three times a day; however, the amount thereof applied may suitably be varied depending upon the magnitude of an affected part, the seriousness of disease, etc.

The present invention will be better understood by the following Examples for the preparation of thermogenic sheet combined poultices and for clinical treatment therewith.

EXAMPLE 1

Preparation of wet pack composition layer:

| | |
|---|---|
| Zinc oxide | 5 Parts by weight |
| Gelatine | 4 Parts by weight |
| Carboxymethylcellulose | 6 Parts by weight |
| Sodium polyacrylate | 4 Parts by weight |
| Glycerine | 30 Parts by weight |
| Water | 48 Parts by weight |

The aforementioned ingredients were kneaded together on a high speed stirrer adjusted to a temperature of 60°–100° C., for 20 minutes to form a plastery blend.

| | |
|---|---|
| Menthol | 13 parts by weight |
| Camphor | 23 parts by weight |
| Methyl salicylate | 30 parts by weight |
| Thymol | 8 parts by weight |
| Peppermint oil | 26 parts by weight |

These ingredients were mixed together to obtain a mixed medicinal fluid which was added to said plastery blend in an amount of 3% by weight of the resulting whole mass. The whole mass was thoroughly kneaded for 10 minutes to obtain a pasty plaster. The pasty plaster so obtained was uniformly spread and coated on flannel in a thickness of about 2 mm, thus forming a wet pack composition layer. The wet pack composition layer so formed was covered with a polyethylene film.

Preparation of thermogenic composition layer:

| | |
|---|---|
| Sodium sulfide pentahydrate | 50.0 Parts by weight |
| Iron carbide | 6.3 Parts by weight |
| Carbon black | 12.5 Parts by weight |
| Cotton linter 15.6 Parts by weight | |
| Sodium sulfate | 15.6 Parts by weight |

Thirty (30) grams of a blend of the above ingredients were pressure molded into a sheet-like shape having an area of 8×12 cm and a bulk density of about 1. The sheet-like molding was attached to a base polyethylene film (70µ thick) with the use of an adhesive and covered with a polyethylene film having a porosity of 3%. The base polyethylene film and porous polyethylene film were heat bonded or sealed to each other around the periphery of the molding by using a usual technique. In addition, the porous polyethylene film was laminated with Japanese paper and flannel.

Preparation of thermogenic sheet combined poultice:

The base polyethylene film to which said thermogenic composition layer was attached, was laminated on its under side with said wet pack composition layer using an adhesive to obtain a thermogenic sheet combined poultice. The poultice so obtained was then wrapped in an air-impermeable packing material.

EXAMPLE 2

Preparation of wet pack composition layer:

| Zinc oxide | 5 Parts by weight |
|---|---|
| Kaoline | 2 Parts by weight |
| Gelatine | 2 Parts by weight |
| Carboxymethylcellulose | 10 Parts by weight |
| Sodium polyacrylate | 2 Parts by weight |
| Glycerine | 15 Parts by weight |
| Sorbitol | 15 Parts by weight |
| Water | 46 Parts by weight |

The above ingredients were kneaded on a high speed stirrer adjusted to 60°–100° C., for 20 minutes to form a plastery blend.

| Menthol | 24 Parts by weight |
|---|---|
| Camphor | 14 Parts by weight |
| Methyl salicylate | 24 Parts by weight |
| Thymol | 2 Parts by weight |
| Peppermint oil | 36 Parts by weight |

These ingredients were mixed with each other to obtain a mixed medicinal fluid which was added to said plastery blend in an amount of 3% by weight of the resulting whole mass. The whole mass was then treated in the same manner as in Example 1 to produce a wet pack composition layer.

Preparation of thermogenic composition layer:

| Potassium sulfide pentahydrate | 37.0 Parts by weight |
|---|---|
| Activated carbon | 18.5 Parts by weight |
| Saw dust | 44.5 Parts by weight |

Thirty (30) grams of a composition consisting of these ingredients, was pressure molded into a sheet (8×12 cm, bulk density of ca 0.1) and attached on one side to a base polyethylene film (70μ thick) with the use of an adhesive and then laminated on the other side with a polyethylene film having a porosity of 3.5%. These base and porous polyethylene films were heat bonded or sealed to each other around the periphery of the sheet-like molding by the use of a usual technique. In addition, said porous polyethylene film was laminated with Japanese paper pores and flannel.

Preparation of thermogenic sheet combined poultice:

A thermogenic sheet combined poultice was prepared in the same manner as in Example 1.

EXAMPLE 3

Preparation of wet pack composition layer:

| Zinc oxide | 10 | Parts by weight |
|---|---|---|
| Gelatine | 8 | " |
| Carboxymethylcellulose | 3 | " |
| Sodium polyacrylate | 0.5 | " |
| Glycerine | 20 | " |
| Sorbitol | 10 | " |
| Water | 45.5 | " |

The above ingredients were kneaded on a high speed stirrer adjusted to 60°–100° C., for 20 minutes thereby obtaining a plastery blend.

| Menthol | 28 Parts by weight |
|---|---|
| Camphor | 28 Parts by weight |
| Methyl salicylate | 19 Parts by weight |
| Thymol | 16 Parts by weight |
| Peppermint oil | 9 Parts by weight |

These ingredients were mixed together thereby obtaining a mixed medicinal fluid. The fluid so obtained was added to the plastery blend in an amount of 3% by weight of the resulting whole mass, and the whole mass so obtained was then treated in the same manner as in Example 1 to obtain a wet pack composition layer.

Preparation of thermogenic composition layer:

| Sodium polysulfide | 62.5 Parts by weight |
|---|---|
| Iron carbide | 18.7 Parts by weight |
| Diatomaceous earth | 18.8 Parts by weight |

Thirty (30) grams of a blend of these ingredients were pressure molded into a sheet-like shape having a size of 8×12 cm and a bulk density of about 1. The sheet-like molding so obtained was attached on one side to a base polyethylene film (70μ thick) with the use of an adhesive and laminated on the other side with a polyethylene film having a porosity of 2.5%. These base and porous polyethylene films were heat sealed to each other around the periphery of the sheet-like molding. In addition, the porous polyethylene film was laminated with Japanese paper and flannel.

Preparation of thermogenic sheet combined poultice:

The preparation was effected in the same manner as in Example 1.

EXAMPLE 4

Preparation of wet pack composition layer:
The following ingredients,

| Zinc oxide | 10 | Parts by weight |
|---|---|---|
| Gelatine | 8 | " |
| Carboxymethylcellulose | 3 | " |
| Sodium polyacrylate | 0.5 | " |
| Glycerine | 20 | " |
| Sorbitol | 10 | " |
| Water | 45.5 | " | were kneaded on a high speed stirrer at an adjusted temperature of 60°–100° C. for 20 minutes to obtain a plastery blend which was incorporated with methyl salicylate in an amount of 3% by weight of the resulting whole mass. The whole mass so obtained was then treated in the same manner as in Example 1 thereby obtaining a wet pack composition layer.

Preparation of thermogenic composition layer and thermogenic sheet combined poultice:

A thermogenic composition layer was prepared in quite the same manner as in Example 1, and a thermogenic sheet combined poultice was prepared by following the procedure of Example 1 except that the above wet pack composition layer was used.

EXAMPLE 5

Preparation of wet pack composition layer:
The following ingredients,

| Zinc oxide | 7 | Parts by weight |
|---|---|---|
| Kaolin | 4 | " |
| Gelatine | 6 | " |

-continued

| | | |
|---|---|---|
| Carboxymethylcellulose | 3 | " |
| Sodium polyacrylate | 2 | " |
| Sorbitol | 30 | " |
| Water | 45 | " | were kneaded on a high speed stirrer at an adjusted temperature of 60°-100° C. for 20 minutes to obtain a blend which was incorporated with the same mixed medicinal fluid as that produced in Example 2 in an amount of 3% by weight of the resulting whole mass. The whole mass so obtained was then treated in the same manner as in Example 1 to obtain a wet pack composition layer.

Preparation of thermogenic composition layer and thermogenic sheet combined poultice:

There was prepared the same thermogenic composition layer as that produced in Example 2.

The wet pack and thermogenic composition layers so obtained were treated in the same manner as in Example 1 to obtain a thermogenic sheet combined poultice.

EXAMPLE 6

Preparation of wet pack composition layer:
The following ingredients,

| | | |
|---|---|---|
| Zinc oxide | 10 | Parts by weight |
| Kaolin | 5 | " |
| Gelatine | 10 | " |
| Carboxymethylcellulose | 8 | " |
| Sodium polyacrylate | 1 | " |
| Glycerine | 15 | " |
| Sorbitol | 15 | " |
| Water | 33 | " | were kneaded together on a high speed stirrer for 20 min. at adjusted temperatures of 60°-100° C. to obtain a blend which was then incorporated with the same mixed medicinal fluid as produced in Example 1, in an amount by weight of 3% of the resulting whole mass. The whole mass so obtained was then treated in the same manner as in Example 1 to prepare a wet pack composition layer.

Preparation of thermogenic composition layer and thermogenic sheet combined poultice:

Quite the same thermogenic composition layer as that produced in Example 3 was prepared, and the thermogenic and wet pack composition layers so prepared were treated in the same manner as in Example 1 to obtain a thermogenic sheet combined poultice.

EXAMPLE 7

Preparation of wet pack composition layer:
The following ingredients,

| | | |
|---|---|---|
| Zinc oxide | 10 | Parts by weight |
| Gelatine | 9 | " |
| Carboxymethylcellulose | 4 | " |
| Sodium polyacrylate | 1.5 | " |
| Glycerine | 20 | " |
| Sorbitol | 10 | " |
| Water | 45.5 | " | were thoroughly kneaded on a high speed stirrer at an adjusted temperature of 60°-100° C. for 25 minutes to obtain a pasty plaster which was then uniformly spread and coated in a thickness of 2 mm on a non-woven cloth. The wet pack composition layer on the non-woven cloth was covered with a polyethylene film.

Preparation of thermogenic composition layer and thermogenic sheet combined poultice:

Quite the same thermogenic composition layer as that produced in Example 1 was obtained. The thermogenic and wet pack composition layers were treated in the same manner as in Example 1 to obtain a thermogenic sheet combined poultice.

EXAMPLE 8

Preparation of wet pack composition layer:
The following ingredients,

| | | |
|---|---|---|
| Zinc oxide | 5 | Parts by weight |
| Gelatine | 3 | Parts by weight |
| Carboxymethylcellulose | 4 | Parts by weight |
| Sodium polyacrylate | 5 | Parts by weight |
| Glycerine | 30 | Parts by weight |
| Sorbitol | 10 | Parts by weight |
| Water | 43 | Parts by weight | were treated in the same manner as in Example 7 to prepare a wet pack composition layer.

Preparation of thermogenic composition layer and thermogenic sheet combined poultice:

There was produced the same thermogenic composition layer as that produced in Example 1. The thermogenic composition layer was then treated, together with the above wet pack composition layer, in the same manner as in Example 1.

EXAMPLE 9

Preparation of wet pack composition layer:

| | | |
|---|---|---|
| Zinc oxide | 5 | Parts by weight |
| Kaolin | 5 | " |
| Gelatine | 6 | " |
| Carboxymethylcellulose | 6 | " |
| Sodium polyacrylate | 3 | " |
| Glycerine | 10 | " |
| Sorbitol | 20 | " |
| Water | 45 | " |

The above ingredients were treated in the same manner as in Example 7 to produce a wet pack composition layer.

Preparation of thermogenic composition layer and thermogenic sheet combined poultice:

Quite the same thermogenic composition layer as that produced in Example 1 was prepared. The thermogenic composition layer was then treated, together with the above wet pack composition layer, in the same manner as in Example 1 to prepare a thermogenic sheet combined poultice.

There will now be explained applications of the thermogenic sheet combined poultices to medical treatment by reference to clinical cases. These poultices used were the same as those prepared in Example 1.

Case 1

A 27-year-old man, with a 3-year history of cervical muscle pain, developed a spasmodic torticollis. The thermogenic sheet combined poultice of the present invention was applied to the cervical part two times (in the morning and evening) a day, thereby relieving the muscle tone and permitting the neck to turn to the affected part 2 or 3 days after the application.

Case 2

8 when they are used in substantially the same manner as in said Cases 1-5.

Table 8

| Case No. | Age | Sex | Disease | Treatment (Use of poultices) | Therapeutic efficacy |
|---|---|---|---|---|---|
| 6 | 21 | M | Lumbodorsodynia | Two times (morning and evening) for 5 days | good |
| 7 | 43 | M | Acute gastrocnemius pain | Two times (morning and evening) for 7 days | excellent |
| 8 | 73 | F | Acute lumbago | Two times (morning and evening) for 7 days | good |
| 9 | 61 | M | Dorsodynia | Two times (morning and evening) for 6 days | fair |
| 10 | 63 | M | Third lumbospondylolisthesis | Two times (morning and evening) for 7 days | good |
| 11 | 45 | F | Dorsodynia | Two times (morning and evening) for 7 days | fair |
| 12 | 26 | F | Tenosynovitis stenosans (De Quervain) | Two times (morning and evening) for 7 days | " |
| 13 | 51 | F | Degeneration of intervertebral disc | Two times (morning and evening) for 7 days | excellent |
| 14 | 57 | M | Psoas pain | Two times (morning and evening) for 5 days | good |
| 15 | 65 | F | Degenerative gonarthropathy | One time (morning and evening) for 5 days | " |
| 16 | 18 | F | Injury of left intra-collateral ligament | One time (morning and evening) for 6 days | " |
| 17 | 43 | F | Right gonalgia | One time (morning and evening) for 7 days | fair |
| 18 | 57 | F | Left gonarthral edema | One time (morning and evening) for 6 days | good |

A 49-year-old woman had sudden attacks of low back pain when she was lifting a heavy weight matter. The pain persisted day and night before the application of the thermogenic sheet combined poultice to the affected part thereby to relieve the pain in a week.

Case 3

A 36-year-old woman complained of a long-lasting smart in the region of the operative wounds after neurolysis and had a hypersensitivity of pressure. The patient was diagnosed as having strangulated ulnar neuritis.

The pain subsided completely during application of the thermogenic sheet combined poultice of the present invention. However, the above complaint re-manifested when said poultice cooled 3 to 4 hours after the application.

Case 4

A 53-year-old man had had a pain in the low back and left hindlimb for more than a year, and was diagnosed as having herniated intervertebral disc and left radicular ischioneuralgia. The pain was mostly relieved during application of the thermogenic sheet combined poultice and the patient's complaint subsided fairly one week after the application.

Case 5

A 77-year-old woman had had a pain in the knee for several years and the edema had appeared for two years before she was diagnosed as having gonalgia deformans and the thermogenic sheet combined poultice of the present invention was applied to the sort part. The pain was mostly relieved after the application of the poultice. One week later, the cinesalgia and tenderness subsided fairly.

Cases 6-18

The thermogenic sheet combined poultices of the present invention exhibited satisfactory medical effects on the various diseases as shown in the following Table

What is claimed is:

1. A thermogenic sheet combined poultice comprising a heat-stable wet pack composition layer and a thermogenic composition layer capable of generating heat in the presence of air or oxygen, the thermogenic composition layer comprising (1) at least one member selected from the group consisting of alkali metal sulfides and polysulfides and the hydrates thereof and (2) at least one member selected from the group consisting of iron carbide and carbonaceous materials.

2. A thermogenic sheet combined poultice according to claim 1, wherein the alkali metal is a member selected from the group consisting of Li, Na, K, Rb and Cs, and the carbonaceous material is a member selected from the group consisting of carbon black, activated carbon, charcoal, coal, coke, pitch, asphalt and graphite.

3. A thermogenic sheet combined poultice according to claim 1, wherein the wet pack composition layer comprises a base ingredient for wet pack and other ingredients necessary therefor.

4. A thermogenic sheet combined poultice according to claim 3, wherein the other ingredient for wet pack is at least one member selected from the group consisting of tackifiers, softening agents and wetting agents.

5. A thermogenic sheet combined poultice according to claim 3, wherein the base ingredient is at least one member selected from the group consisting of kaolin, bentonite, talc, wax, vaseline, sodium lactate, zinc oxide, boric acid and aluminum silicate, and the other ingredient is at least one member selected from the group consisting of sodium alginate, methylcellulose, carboxyvinyl polymers, carboxymethylcellulose, ethylcellulose, polyvinylpyrrolidone, polyvinyl alcohol, polyvinyl methyl ether, sodium polyacrylate, tragacanth gum, atactic polypropylene, guaiachol, ester gum, natural rubber latex, gelatine, fluid paraffin, silicone, glycerine, propylene glycol, polyethylene glycol, diethyl glycol monoethyl ether, magnesium oxide, sorbitol, xylytol, urea, aluminum acetate, beryllium hydroxide, magnesium hydroxide, calcium hydroxide, barium hydroxide and water.

6. A thermogenic sheet combined poultice according to claim 3, wherein the wet pack composition layer comprises, by weight, 2-21 parts of the base ingredient for wet pack and 79-97 parts of the other ingredients for wet pack.

7. A thermogenic sheet combined poultice according to claim 1, wherein the wet pack composition layer comprises a base ingredient for wet pack, other ingredients necessary for wet pack, and a medicine for wet pack.

8. A thermogenic sheet combined poultice according to claim 7, wherein the other ingredient for wet pack is at least one member selected from the group consisting of tackifiers, softening agents and wetting agents.

9. A thermogenic sheet combined poultice according to claim 7, wherein the base ingredient is at least one member selected from the group consisting of kaolin, bentonite, talc, wax, vaseline, sodium lactate, zinc oxide, boric acid and aluminum silicate; the other ingredient is at least one member selected from the group consisting of sodium alginate, methylcellulose, carboxyvinyl polymers, carboxymethylcellulose, ethylcellulose, polyvinylpyrrolidone, polyvinyl alcohol, polyvinyl methyl ether, sodium polyacrylate, tragacanth gum, atactic polypropylene, guaiachol, ester gum, natural rubber latex, gelatine, fluid paraffin, silicone, glycerine, propylene glycol, polyethylene glycol, diethyl glycol monoethyl ether, magnesium oxide, sorbitol, xylytol, urea, aluminum acetate, beryllium hydroxide, magnesium hydroxide, calcium hydroxide, barium oxide and water; and the medicine for wet pack is at least one member selected from the group consisting of methyl salicylate, salicylic acid glycol, salicylic acid, menthol, peppermint oil, camphor, thymol, creosote, taurine, extract of scopolia, diphenylhydramine hydrochloride, diphenylhydramine, mercurochrome, burn phellodendron bark, pickled plum flesh, Japanese pepper oil, borneol, epirocaine and mixtures thereof.

10. A thermogenic sheet combined poultice according to claim 7, wherein the wet pack composition layer comprises, by weight, 3-20 parts of the base ingredient for wet pack, 76-96 parts of the other ingredients for wet pack and 1-4 parts of the medicine for wet pack.

* * * * *